United States Patent
Wang

(10) Patent No.: US 11,834,496 B2
(45) Date of Patent: Dec. 5, 2023

(54) COMPOSITION OF A DRUG CARRIER, PHARMACEUTICAL COMPOSITION THEREOF, PREPARATION METHOD AND USE METHOD THEREOF

(71) Applicant: EOS BIOMATERIALS INC., New Taipei (TW)

(72) Inventor: Chung-Hao Wang, New Taipei (TW)

(73) Assignee: EOS BIOMATERIALS INC., New Taipei (TW)

( * ) Notice: Subject to any disclaimer, the term of this patent is extended or adjusted under 35 U.S.C. 154(b) by 274 days.

(21) Appl. No.: 17/121,794

(22) Filed: Dec. 15, 2020

(65) Prior Publication Data

US 2021/0309731 A1 Oct. 7, 2021

Related U.S. Application Data

(60) Provisional application No. 63/003,912, filed on Apr. 2, 2020.

(51) Int. Cl.
| | |
|---|---|
| A61L 24/00 | (2006.01) |
| C07K 16/24 | (2006.01) |
| A61K 31/4025 | (2006.01) |
| A61K 31/43 | (2006.01) |
| A61K 31/431 | (2006.01) |
| A61K 31/546 | (2006.01) |
| A61K 31/575 | (2006.01) |
| A61K 31/702 | (2006.01) |
| A61K 38/12 | (2006.01) |
| A61K 38/14 | (2006.01) |
| A61K 38/17 | (2006.01) |
| A61K 47/02 | (2006.01) |
| A61K 47/32 | (2006.01) |
| A61K 47/36 | (2006.01) |
| A61K 47/38 | (2006.01) |
| A61K 47/42 | (2017.01) |
| C07K 16/28 | (2006.01) |
| A61K 39/00 | (2006.01) |
| A61K 31/7036 | (2006.01) |
| A61K 39/395 | (2006.01) |

(52) U.S. Cl.
CPC ........ *C07K 16/241* (2013.01); *A61K 31/4025* (2013.01); *A61K 31/43* (2013.01); *A61K 31/431* (2013.01); *A61K 31/546* (2013.01); *A61K 31/575* (2013.01); *A61K 31/702* (2013.01); *A61K 38/12* (2013.01); *A61K 38/14* (2013.01); *A61K 38/1774* (2013.01); *A61K 38/1793* (2013.01); *A61K 47/02* (2013.01); *A61K 47/32* (2013.01); *A61K 47/36* (2013.01); *A61K 47/38* (2013.01); *A61K 47/42* (2013.01); *C07K 16/2866* (2013.01); *C07K 16/2887* (2013.01); *A61K 31/7036* (2013.01); *A61K 39/395* (2013.01); *A61K 2039/505* (2013.01); *C07K 2317/21* (2013.01); *C07K 2317/24* (2013.01); *C07K 2317/55* (2013.01)

(58) Field of Classification Search
CPC ............ A61L 24/0047; A61L 24/0057; A61L 24/0063; A61L 24/0084; A61L 24/0094
See application file for complete search history.

(56) References Cited

U.S. PATENT DOCUMENTS

| | | | |
|---|---|---|---|
| 2007/0059281 A1* | 3/2007 | Moseley | A61L 27/365 424/602 |
| 2007/0254042 A1* | 11/2007 | Drapeau | A61L 27/48 424/550 |
| 2013/0287817 A1* | 10/2013 | Drapeau | A61L 27/54 514/169 |
| 2019/0076570 A1* | 3/2019 | Shao | A61L 24/0094 |

* cited by examiner

*Primary Examiner* — Micah Paul Young

(57) ABSTRACT

A composition of a drug carrier, a pharmaceutical composition thereof, a preparation method and a use method thereof are provided. The composition of a drug carrier includes a first mixture and a second mixture. The first mixture includes a hydrophilic polymer, tricalcium phosphate and a water-soluble dispersant. The second mixture includes a water-absorbing material and a divalent cation salt. The pharmaceutical composition includes the composition of a drug carrier above and a drug for preparing an anti-inflammatory or antibiotic medicine. The preparation method of the composition of a drug carrier includes mixing the first mixture and the second mixture. The use method of the composition of a drug carrier includes mixing the first mixture with a drug and then adding the second mixture. Accordingly, topically applying the pharmaceutical composition on a surgical site may effectively release the drug thereon.

7 Claims, 4 Drawing Sheets

COMPOSITION OF A DRUG CARRIER, PHARMACEUTICAL COMPOSITION THEREOF, PREPARATION METHOD AND USE METHOD THEREOF

CROSS-REFERENCE TO RELATED APPLICATIONS

This application claims the benefit of U.S. Provisional Application No. 63/003,912, filed on Apr. 2, 2020, the contents of which are incorporated herein by reference in their entireties.

BACKGROUND

Technical Field

This disclosure relates to a composition for prerparing a drug carrier and a pharmaceutical composition, as well as a preparation method and a use method thereof. Particularly, this disclosure relates to a drug carrier that may effectively release drugs at surgical sites.

Description of the Related Art

In the current field of drug release technology, one of the main research directions is to achieve the expected drug release effect through the design of the drug carrier. Most prior arts use proteins, amino acids and some other biopolymers to prepare drug carriers, and the biopolymers are commonly used materials among them. Biopolymers need to be biocompatible and biodegradable. "Biocompatibility" means that the material is compatible with the biological individual and will not cause immune rejection or pathological changes. At the same time, it will not cause or cause cardiovascular embolism, toxic reactions, allergic reactions, tissue destruction and carcinogenesis during use. "Biodegradability" refers to the phenomenon that when a material is implanted or used in an organism, the material will undergo hydrolysis or oxidation in the biological environment, causing the material to disintegrate or decompose into other products. In addition, the products of the disintegration or decomposition may be further decomposed and discharged from the organism through the basic metabolism of the organism. Biopolymers may be divided into natural polymers and synthetic polymers. The common natural polymers include chitosan, alginate, chitin, collage, hyaluronic acid and other materials.

On the other hand, in orthopedic surgery, drug release is also an important issue. For example, in artificial joint replacement surgery, the probability of postoperative infection is about 2 to 3%. Among them, the greatest risk of postoperative infection is the deep-seated infection of the operation. If it is not handled properly, it will require multiple operations or long-term antibiotic treatment. In order to reduce the risk of inflammation caused by deep infection, there is currently a method to add antibiotics to the implanted bone filling material, and then the antibiotic is released through the implanted bone filling material to the part where deep infection may occur.

SUMMARY

However, the release of antibiotics through the implanted bone filling material to reduce the risk of inflammation caused by deep infection will cause another problem. After antibiotics are added to the bone filling material, the durability of the bone filling material is significantly reduced. This may lead to the risk of shaking or displacement of the implant in the later stage of recovery. In order to solve the problem of the reduced durability of bone filling materials after antibiotics are added, another alternative method uses traditional injection methods to administer antibiotics. Usually the antibiotics are injected into a patient's wrist vein, and then delivered to the surgical site through the systemic blood circulation. However, this method may not completely and effectively deliver antibiotics to the surgical site.

In view of the above-mentioned problems, an embodiment of this invention provides a composition, for preparing a drug carrier, includes a first mixture and a second mixture. The first mixture comprises 300 to 3600 parts by weight of a hydrophilic polymer, 300 to 3600 parts by weight of tricalcium phosphate, and 100 to 1800 parts by weight of a water-soluble dispersant. The second mixture comprises 100 to 7200 parts by weight of a water-absorbing material, and 10 to 1800 parts by weight of a divalent cation salt. The water-absorbing material has high biocompatibility, high hygroscopicity, and biodegradability.

In the composition for preparing a drug carrier as described above, the tricalcium phosphate is α-phase tricalcium phosphate or β-phase tricalcium phosphate.

In the composition for preparing a drug carrier as described above, the water-soluble dispersant is selected from the group consisting of methyl cellulose (MC), carboxymethyl cellulose (CMC), hydroxyethyl cellulose (HEC), hydroxypropyl methyl cellulose (HPMC), and any combinations thereof.

In the composition for preparing a drug carrier as described above, the water-absorbing material is selected from the group consisting of hyaluronic acid (HA), sodium hyaluronate, collagen, gelatin, polydextrose, and any combinations thereof.

In the composition for preparing a drug carrier as described above, the divalent cationic salt is selected from the group consisting of calcium chloride ($CaCl_2$), calcium carbonate ($CaCO_3$), barium chloride ($BaCl_2$), strontium chloride ($SrCl_2$), magnesium chloride ($MgCl_2$), and any combinations thereof.

In order to achieve the above and other aspects, another embodiment of this invention provides a pharmaceutical composition for preparing anti-inflammatory or antibiotic drugs using the drug carrier prepared by the above composition for preparing a drug carrier.

In order to achieve the above and other aspects, still another embodiment of this invention provides a method of preparing a pharmaceutical composition. The method comprises following steps. A first mixture is prepared by mixing 300 to 3600 parts by weight of a hydrophilic polymer, 300 to 3600 parts by weight of tricalcium phosphate, and 100 to 1800 parts by weight of a water-soluble dispersant. A second mixture is prepared by mixing 100 to 7200 parts by weight of a water-absorbing material, and 10 to 1800 parts by weight of a divalent cationic salt, wherein the water-absorbing material is biocompatible and biodegradable. A precursor mixture is then prepared by mixing a drug and the first mixture in water. The second mixture and the precursor mixture are then mixed to obtain a pharmaceutical composition.

In order to achieve the above and other aspects, still another embodiment of this invention provides a pharmaceutical composition prepared by the above method of preparing a pharmaceutical composition.

In the pharmaceutical composition as described above, the drug may be an anti-inflammatory drug or an antibiotic.

The anti-inflammatory drug may be selected from the group consisting of adalimumab, certolizumab, etanercept, golimumab, abatacept, tocilizumab, rituximab, infliximab, and any combinations thereof. The antibiotic may be selected from the group consisting of gentamicin, vancomycin, mezlocillin, cloxacillin, methicillin, cefalothin, lincomycin, polymyxin E, bacitracin, fusidic acid, and any combinations thereof.

In light of the foregoing, a drug may be effectively released at a surgical site when the pharmaceutical composition is applied on the surgical site.

DETAILED DESCRIPTION

Figure 1:
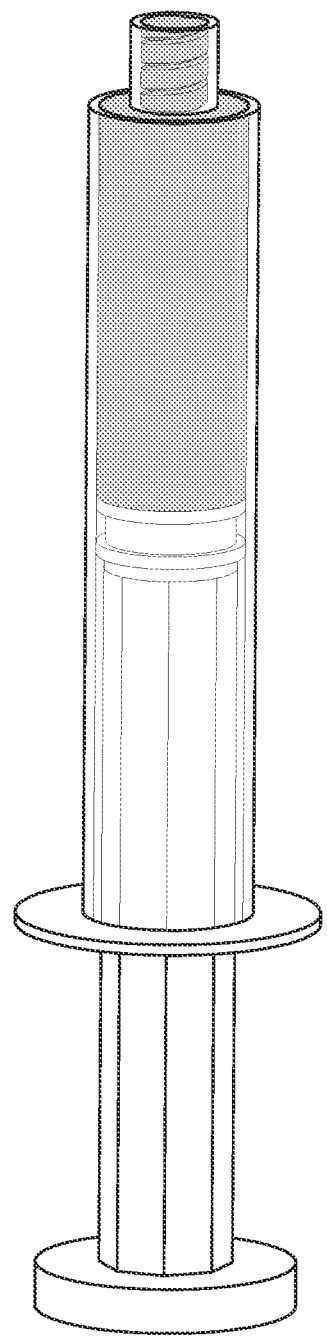
FIG. 1 shows an appearance of a drug carrier of Example 1 in a syringe.

Reference will now be made in detail to the present embodiments of the invention, examples of which are illustrated in the accompanying drawings. For illustration clarity, many details of practice are explained in the following descriptions. However, it should be understood that these details of practice do not intend to limit the present invention. That is, these details of practice are not necessary in parts of embodiments of the present invention. Furthermore, for simplifying the drawings, some of the conventional structures and elements are shown with schematic illustrations.

Composition for Preparing Drug Carrier

In this embodiment, a composition for preparing a drug carrier comprises a first mixture and a second mixture. The composition is prepared by the following method.

The first mixture comprises 300 to 3600 parts by weight of a hydrophilic polymer, 300 to 3600 parts by weight of tricalcium phosphate ($Ca_3(PO_4)_2$), and 100 to 1800 parts by weight of a water-soluble dispersant. The second mixture comprises 100 to 7200 parts by weight of a water-absorbing material, and 10 to 1800 parts by weight of a divalent cationic salt. The water-absorbing material is biocompatible and biodegradable.

In some embodiments of this invention, the hydrophilic polymer has at least one anionic group, such as a carboxylate group. The hydrophilic polymer may be a salt of alginatic acid, polyacrylic acid, gelatin, carboxymethyl cellulose (CMC), polyglutamatic acid (γ-PGA), or any combinations thereof, with a monovalent metal cation such as $Na^+$ or $K^+$. However, in some other embodiments of this invention, the hydrophilic polymer may also be replaced by other hydrophilic polymers with similar properties and thus is not limited thereto. The parts by weight of the hydrophilic polymer may be 300, 400, 600, 1000, 1200, 1500, 1800, 2000, 2500, 2800, 3000, or 3600, but the parts by weight of the hydrophilic polymer is not limited to the above specific values.

In some embodiments of this invention, the tricalcium phosphate is α-phase tricalcium phosphate or β-phase tricalcium phosphate. The parts by weight of the tricalcium phosphate may be 300, 600, 1000, 1200, 1500, 1800, 2000, 2500, 2800, 3000, or 3600, but the parts by weight of the tricalcium phosphate is not limited to the above specific values.

In some embodiments of this invention, the water-soluble dispersant may be methyl cellulose (MC), carboxymethyl cellulose (CMC), hydroxyethyl cellulose (HEC), hydroxypropyl methyl cellulose (HPMC), or any combinations thereof. However, in some other embodiments, the water-soluble dispersant may also be replaced by other water-soluble dispersants with similar properties and thus is not limited thereto. The parts by weight of the water-soluble dispersant may be 100, 200, 300, 400, 800, 1200, 1600, or 1800, but the parts by weight of the water-soluble dispersant is not limited to the above specific values.

In some embodiments of this invention, the water-absorbing material may be hyaluronic acid (HA), sodium hyaluronate, collagen, gelatin, polydextrose, or any combinations thereof. The water-absorbing material may absorb a lot of water as well as is biocompatible and biodegradable. However, in some other embodiments, the water-absorbing material may also be replaced by other water-absorbing materials with similar properties and thus is not limited thereto. The parts by weight of the water-absorbing material may be 100, 500, 1000, 1500, 2000, 3000, 4000, 5000, 6000, or 7200, but the parts by weight of the water-absorbing material is not limited to the above specific values.

In some embodiments of this invention, the divalent cationic salt may be calcium chloride ($CaCl_2$), calcium carbonate ($CaCO_3$), strontium chloride ($SrCl_2$), barium chloride ($BaCl_2$), magnesium chloride ($MgCl_2$), or any combinations thereof. However, in some other embodiments, the divalent cationic salt may also be replaced by other divalent cationic salts with similar properties and thus is not limited thereto. The parts by weight of the divalent cationic salt may be 10, 50, 100, 200, 300, 400, 500, 1000, 1200, 1600, or 1800, but the parts by weight of the divalent cationic salt is not limited to the above specific values. The divalent cation of the divalent cationic salt may act as a cross-linking agent of the salt form of the hydrophilic polymer.

In some other embodiments, the first mixture and the second mixture may further comprise 5,000 to 90,000 and 2,000 to 180,000 parts by weight of water, respectively.

Method of Preparing Composition for Preparing Drug Carrier

In this method, the first mixture above is prepared by the following steps. 300 to 3600 parts by weight of a hydrophilic polymer, 300 to 3600 parts by weight of tricalcium phosphate ($Ca_3(PO_4)_2$), and 100 to 1800 parts by weight of a water-soluble dispersant are dispersed and mixed in water. The water-soluble dispersant may promote the uniform mixing of the hydrophilic polymer and tricalcium phosphate. After mixing, hydrogen bondings may be generated in a single molecule of the hydrophilic polymer and between different molecules of the hydrophilic polymer as well as between the molecules of the hydrophilic polymer and the phosphate anions of tricalcium phosphate to form a network structure.

After the first mixture is prepared, the first mixture may be further dried to be more stably stored. For example, the first mixture may be further dried into a dry batt block material by freeze drying. However, the first mixture may also be stored in the original solution form, and thus the storage form of the first mixture is not limited as long as the storage stability of the first mixture is acceptable.

The second mixture above is prepared by the following steps. 100 to 7200 parts by weight of a water-absorbing material and 10 to 1800 parts by weight of a divalent cationic salt may be respectively dissolved in water and then mixed. Alternatively, the water-absorbing material also may be directly dissolved in a solution of the divalent cation salt.

Drug Carrier

In some embodiments, a drug carrier is also provided. The composition of a drug carrier comprises 300-3600 parts by weight of a hydrophilic polymer, 300-3600 parts by weight of tricalcium phosphate, 100-1800 parts by weight of a water-soluble dispersant, 100-7200 parts by weight of a water-absorbing material, and 10-1800 parts by weight of a divalent cationic salt. The details of the hydrophilic polymer, the water-soluble dispersant, the water-absorbing material, and the divalent cationic salt have been described above and thus omitted here.

In some other embodiments, the composition of the drug carrier may further comprise 7,000 to 270,000 parts by weight of water.

Method of Preparing Drug Carrier

In this method, the drug carrier above is prepared by the following steps. First, the first mixture and the second mixture are respectively prepared as stated above. Then, the first mixture and the second mixture are further uniformly mixed to obtain the drug carrier above, so that the hydrophilic polymer in the first mixture can be cross-linked by the divalent cations in the second mixture to form a drug carrier in a gel form.

Examples 1-3 of Preparing Drug Carriers

In these examples, drug carriers with different compositions were prepared by the method of preparing drug carriers, as stated above.

In the first mixture of Examples 1-3, the hydrophilic polymer was alginate, and the water-soluble dispersant was methyl cellulose. The mixing ratios of alginate, tricalcium phosphate, and methyl cellulose in Examples 1-3 are listed in Table 1 below. Thus, alginate, tricalcium phosphate, and methyl cellulose in ratios listed in Table 1 were first dispersed in water and then mixed to prepare the first mixtures of Examples 1-3, respectively.

TABLE 1

The parts by weight of each component in the first mixtures of Examples 1-3[#]

|  | Alginate | Tricalcium Phosphate | Methyl Cellulose |
|---|---|---|---|
| Example 1 | 1200 | 1200 | 200 |
| Example 2 | 600 | 600 | 200 |
| Example 3 | 300 | 300 | 200 |

Unit: parts by weight
[#]Examples 1-3 were dispersed in 6500 parts by weight of water, respectively.

In the second mixture of Examples 1-3, the water-absorbing material was sodium hyaluronate, and the divalent cationic salt was calcium chloride in a form of an aqueous solution having a concentration of 30 mg/mL. The mixing ratios of sodium hyaluronate and calcium chloride are listed in Table 2 below. Thus, sodium hyaluronate was dissolved in the aqueous solutions of calcium chloride, in ratios listed in Table 2, to prepare the second mixtures of Examples 1-3, respectively.

TABLE 2

The parts by weight of each component in the second mixtures of Examples 1-3[#]

|  | Sodium hyaluronate | Calcium chloride (aq.)* |
|---|---|---|
| Example 1 | 1000 | 400 |
| Example 2 | 1000 | 400 |
| Example 3 | 1000 | 400 |

Unit: parts by weight
*concentration: 30 mg/mL
[#]Examples 1-3 were dispersed in 13000 parts by weight of water, respectively.

Finally, in Examples 1-3, the first mixtures and the second mixtures are uniformly mixed, respectively, an then drug carriers in the gel form were obtained.

FIG. 1 shows an appearance of a drug carrier of Example 1 in a syringe. In FIG. 1, the drug carrier prepared in Example 1 was in a form of a milky white gel. The appearances of the drug carriers prepared in Examples 2 and 3 were also the same as the appearance of the drug carrier prepared in Example 1.

Figure 2:
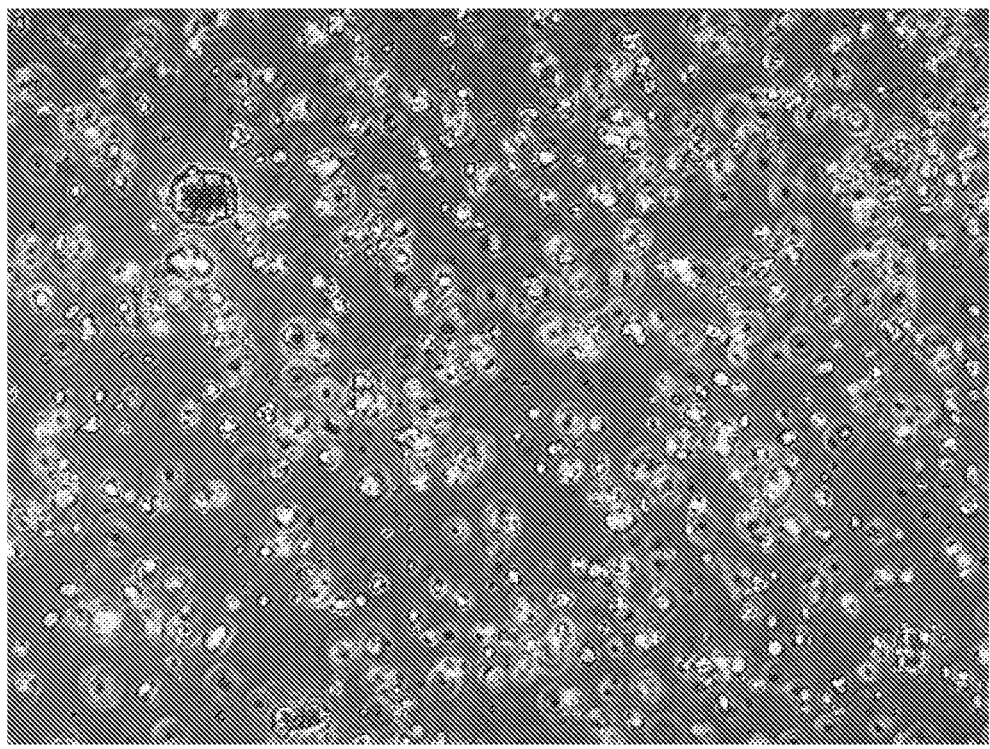
FIG. 2 is an optical image showing the distribution of particles of the drug carrier of Example 1 observed with an inverted microscope.

FIG. 2 is an optical image showing the distribution of particles of the drug carrier of Example 1 observed with an inverted microscope (ECLIPSE Ts2, NIKON) at the magnification of an eyepiece 10 times and an objective lens 20 times. In FIG. 2, the particles in the drug carrier of Example 1 were in a state of uniformly dispersed.

Biocompatibility Test of Composition of a Drug Carrier:

First, the gel-form drug carriers of Examples 1-3 were respectively prepared by the preparation method described above.

Then, four 6-well plates were prepared. In each of the 6-well plates, 2 ml of a cell culture solution containing NIH/3T3 cells in culture medium were added to three wells of each 6-well plate. The culture medium was DMEM medium, and the concentration of the NIH/3T3 cells was $1 \times 10^5$ cells/ml.

Next, three wells of the first, second, and the third 6-well plates were respectively added with the drug carriers of Examples 1, 2, and 3, and the added amount of the drug carriers were 20 μL. The first, second, and third 6-well plates added with drug carriers were to be the experimental groups 1, 2, and 3, respectively. Three wells of the fourth plate were not added with any drug carriers, and thus the fourth plate was to be the control group.

TABLE 3

The added amount of drug carriers and cell culture solutions.

| Drug Carrier | Ex. 1 | Ex. 2 | Ex. 3 | $1 \times 10^5$ NIH/3T3 cells / 1 mL DMEM medium |
|---|---|---|---|---|
| Exp. 1 | 20 μL | — | — | 2 mL |
| Exp. 2 | — | 20 μL | — | 2 mL |
| Exp. 3 | — | — | 20 μL | 2 mL |
| Control | — | — | — | 2 mL |

Finally, the 6-well plates of experimental groups 1-3 and the control group were placed into a cell incubator and incubated at 37° C. for 48 hours. Each well of the experimental groups 1-3 and the control group was sampled 100 μl of cell culture solution at the 24th and 48th hour. The sampled cell culture solutions of the experimental groups 1-3 and the control group were subjected to the MTT test with tetramethylazolium salt solution (MTT, 3-(4,5-Dimethylthiazol-2-yl)-2,5-diphenyltetrazolium bromide). Based on the results of the MTT test, the average cell survival rates of the experimental groups 1-3 and the control group were calculated.

Figure 3:
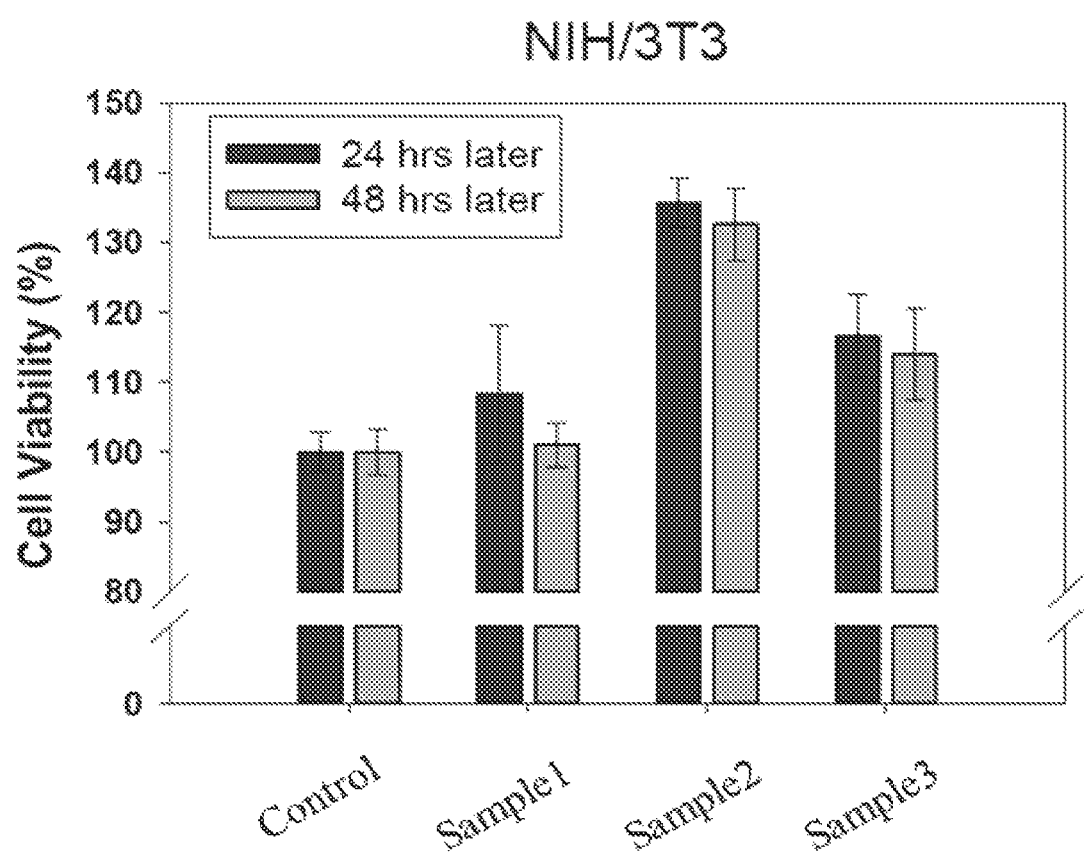
FIG. 3 shows the cell viability analysis results of the drug carriers in the biocompatibility test.

FIG. 3 shows the cell viability analysis results of the drug carriers in the biocompatibility test. In FIG. 3, after culturing for 24 or 48 hours, the cell numbers in the experimental groups 1-3 were more than the cell number in the control group. Comparing with the cell numbers obtained at 24 hours, the cell numbers at 48 hours were all decreased in the experimental groups 1-3, since the increase of cell concentration caused the deterioration of the culture environment. Therefore, it may be seen that the drug carriers in Examples 1-3 not only is highly biocompatible and non-toxic but also may promote cell growth.

Method of Preparing Pharmaceutical Composition

In some embodiment, a pharmaceutical composition is further provided and prepared by the following method. The pharmaceutical composition comprises the composition of the drug carrier above and a drug.

First, the first mixture above is prepared by mixing 300 to 3600 parts by weight of a hydrophilic polymer, 300 to 3600 parts by weight of tricalcium phosphate, and 100 to 1800 parts by weight of a water-soluble dispersant.

Next, the second mixture above is prepared by mixing 100 to 7200 parts by weight of a water-absorbing material and 10 to 1800 parts by weight of a divalent cationic salt.

Then, a precursor mixture is prepared by mixing a drug and the first mixture in water.

Finally, the second mixture and the precursor mixture are mixed to form the pharmaceutical composition.

Although the drug is mixed with the first mixture first for more effectively embedding the drug, the drug may be also mixed with the first mixture and the second mixture at the same time. Therefore, the mixing sequence is not limited to the method above.

In some embodiments, the drug above may be an anti-inflammatory drug or an antibiotic. The anti-inflammatory drug may be adalimumab, certolizumab, etanercept, golimumab, abatacept, tocilizumab, rituximab, infliximab, and any combinations thereof. The antibiotic is selected from the group consisting of gentamicin, vancomycin, mezlocillin, cloxacillin, methicillin, cefalothin, lincomycin, polymyxin E, bacitracin, fusidic acid, and any combinations thereof. However, in some other embodiments, the drug may also be replaced by other drugs with similar properties and is not limited thereto. The parts by weight of the drug may be 30-300, such as 80-200. For example, the parts by weight of the drug may be 30, 40, 60, 80, 100, 120, 140, 160, 180, 200, 220, 240, 260, 280, or 300. The parts by weight of the drug are not limited to the above-specified values.

Since the hydrophilic polymer and tricalcium phosphate in the first mixture forms a network structure through hydrogen bondings, the drug may be dispersed and entangled in the network structure. In addition, since the divalent cations provided by the divalent cation salts in the second mixture further cross-link the hydrophilic polymer to make the pharmaceutical composition in a gel form, the drug may be more effectively retained in the network structure of the drug carrier. Hence, the drug may be carried by the drug carrier and released in a human body.

Drug Release Rate Test of Pharmaceutical Composition

In this test, a total of 3 ml solutions of the first and second mixtures (the weight ratio of sodium alginate:tricalcium phosphate:methylcellulose:sodium hyaluronate:calcium chloride was 36:36:15:80:20) and 50 mg of gentamicin were mixed to prepare a pharmaceutical composition containing gentamicin to be an experimental group. Then, the pharmaceutical composition containing gentamicin was placed in a dialysis bag. At the same time, 50 mg of gentamicin was dissolved in 3 ml of water as a control group.

Next, two 500 ml beaker were respectively added with 200 ml of phosphate buffered saline (PBS) solution. The prepared solutions of the experimental group and control group were respectively placed in dialysis bags, which were then placed in the PBS solutions. After that, the beakers, containing the dialysis bag and the PBS solution, were slightly shaken at 37° C. to allow the release of the drug from the dialysis bag to the PBS solution. In the drug release period, the PBS solution of the experimental and control groups are sampled at 15 minutes, 30 minutes, 45 minutes, 60 minutes, 75 minutes, 90 minutes, 105 minutes, 120 minutes, 150 minutes, 180 minutes, 1 day, 2 days, 3 days, 4 days, 5 days, 6 days, and 7 days, from the time start shaking. The sampled volume of the PBS solutions in beakers was 1 mL, and 1 mL of fresh PBS solution was added back to the sampled beakers. The concentrations of the gentamicin released in the PBS solution from the dialysis bag were analyzed by high performance liquid chromatography (HPLC).

Figure 4A:
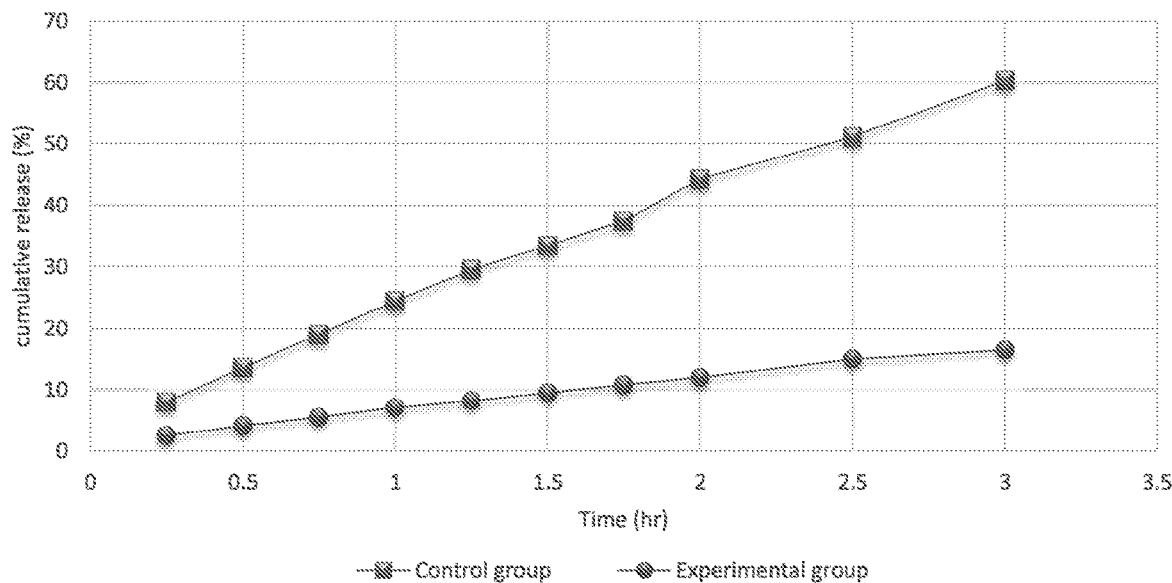
FIGS. 4A and 4B show the results of the drug release rate of the experimental group and the control group within 3 and 180 hours, respectively.
Figure 4B:
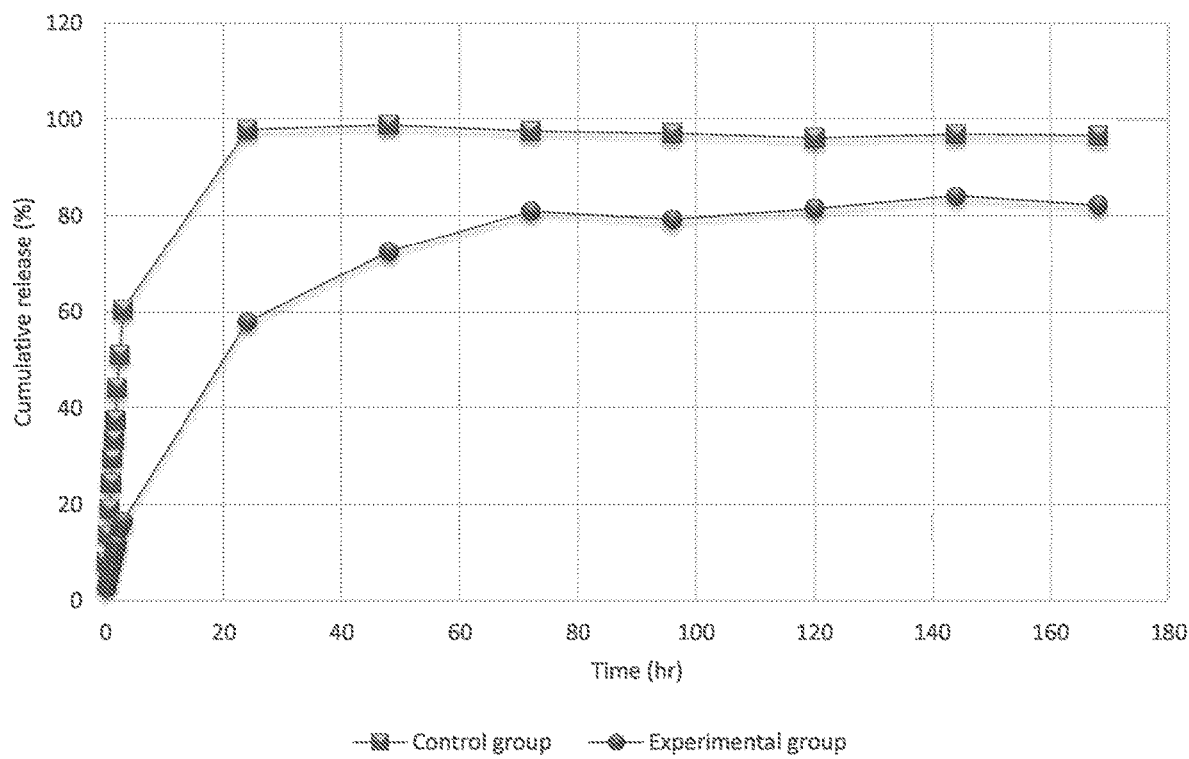

FIGS. 4A and 4B show the results of the drug release rate of the experimental group and the control group within 3 and 180 hours, respectively. In FIG. 4A, the drug release rate of the control group was much faster than the drug release rate of the experimental group within the first 3 hours. In the first 3 hours, the release rate of gentamicin in the experimental group is quite slow within the first 3 hours.

In FIG. 4B, the drug release rate of the control group was still much faster than the drug release rate of the experimental group within 180 hours. For the control group, the cumulative release amount of the gentamicin released in the PBS solution reach almost 100% in less than 30 hours. For the experimental group, the cumulative release amount of the gentamicin released in the PBS solution slowly reach about 80% after 70 hours. Therefore, the pharmaceutical composition in this embodiment may prolong the release time and residence time of the drug in a human body.

In light of the foregoing, the pharmaceutical composition containing the above drug carrier may be topically applied to a needed part of a human body, such as applied to a surgically affected part of a patient, to slowly release the drug in the pharmaceutical composition to the needed part of the human body in a relatively long period. Therefore, the effect of the drug on the needed part of the human body can be greatly increased in a relatively long period without affecting other parts surrounding the needed parts of the human body, compared with the conventional injection method. The other parts surrounding the needed parts of the human body may be an implanted site of a prosthesis in a bone tissue, for example. Hence, the pharmaceutical composition has a higher safety to the human body.

In addition to be directly applied to an affected part of a patient undergoing orthopedic surgery, the pharmaceutical composition may also be coated on a surface of an implantable medical device, such as an implantable prosthesis, a metal implant material, and an implantable fixed medical device used in orthopedic surgery. A method of coating the pharmaceutical composition on the above-mentioned medical device comprises the following steps. The medical device may be immersed in the pharmaceutical composition above and then in a 10-30 mg/mL solution of a divalent cation salt, such as calcium chloride to increase the cross-linking degree of the hydrophilic polymer. Hence, the hardness of the pharmaceutical composition ciated on the surface of the medical device may be further increased.

Moreover, because the water-absorbing material of the drug carrier is biodegradable and other components of the drug carrier are also biocompatible, the drug carrier may be degraded in a human body and discharged from the human body within a certain period of time without affecting the health of the human body.

The present invention has been disclosed in a preferred embodiment above, but those skilled in the art should understand that the embodiment is only used to describe the present invention and should not be construed as limiting the scope of the present invention. It should be noted that all changes and substitutions equivalent to this embodiment should be included in the scope of the present invention. Therefore, the protection scope of the present invention should be defined by the scope of the patent application.

What is claimed is:

1. A method for preparing a pharmaceutical composition, the method comprising:
    preparing a first mixture by uniformly mixing 300 to 3600 parts by weight of a hydrophilic polymer, 300 to 3600 parts by weight of tricalcium phosphate, and 100 to 1800 parts by weight of a water-soluble dispersant, wherein the hydrophilic polymer is selected from the group consisting of a salt of alginic acid, polyacrylic acid and polyglutamic acid (γ-PGA), and wherein the water-soluble dispersant is selected from the group consisting of methyl cellulose (MC), carboxymethyl cellulose (CMC), hydroxyethyl cellulose (HEC) and hydroxypropyl methyl cellulose (HPMC);
    preparing a second mixture by uniformly mixing 100 to 7200 parts by weight of a water-absorbing material, and 10 to 1800 parts by weight of a divalent cationic salt, wherein the water-absorbing material has high biocompatibility, moisture content and degradable property, wherein the water-absorbing material is selected from the group consisting of hyaluronic acid (HA), sodium hyaluronate, collagen, gelatin and polydextrose, and wherein the divalent cationic salt is selected from the group consisting of calcium chloride ($CaCl_2$), calcium carbonate ($CaCO_3$), barium chloride ($BaCl_2$), strontium chloride ($SrCl_2$) and magnesium chloride ($MgCl_2$);
    preparing a precursor mixture by uniformly mixing a drug and the first mixture in water; and
    uniformly mixing the second mixture and the precursor mixture.

2. The method of claim 1, wherein the tricalcium phosphate is α-phase tricalcium phosphate or β-phase tricalcium phosphate.

3. The method of claim 1, wherein the drug is an anti-inflammatory drug or an antibiotic, wherein
    the anti-inflammatory drug is selected from the group consisting of adalimumab, certolizumab, etanercept, golimumab, abatacept, tocilizumab, rituximab and infliximab; and
    the antibiotic is selected from the group consisting of gentamicin, vancomycin, mezlocillin, cloxacillin, methicillin, cefalothin, lincomycin, polymyxin E, bacitracin and fusidic acid.

4. A pharmaceutical composition prepared by the method of claim 1.

5. The pharmaceutical composition of claim 4, wherein the drug is an anti-inflammatory drug or an antibiotic.

6. The pharmaceutical composition of claim 5, wherein the anti-inflammatory drug is selected from the group consisting of adalimumab, certolizumab, etanercept, golimumab, abatacept, tocilizumab, rituximab and infliximab.

7. The pharmaceutical composition of claim 5, wherein the antibiotic is selected from the group consisting of gentamicin, vancomycin, mezlocillin, cloxacillin, methicillin, cefalothin, lincomycin, polymyxin E, bacitracin and fusidic acid.

* * * * *